United States Patent
Hamlin et al.

(10) Patent No.: US 12,036,124 B2
(45) Date of Patent: Jul. 16, 2024

(54) PUMP HAVING A VOLUME AMPLIFICATION MECHANISM FOR AN INFLATABLE PENILE PROSTHESIS

(71) Applicant: Coloplast A/S, Humlebaek (DK)

(72) Inventors: Frederick William Hamlin, Cambridge (GB); Anna Christina Miller, Anchorage, AK (US); John J. Allen, Mendota Heights, MN (US)

(73) Assignee: Coloplast A/S, Humlebaek (DK)

( * ) Notice: Subject to any disclaimer, the term of this patent is extended or adjusted under 35 U.S.C. 154(b) by 256 days.

(21) Appl. No.: 17/666,581

(22) Filed: Feb. 8, 2022

(65) Prior Publication Data

US 2022/0249234 A1 Aug. 11, 2022

Related U.S. Application Data

(60) Provisional application No. 63/149,691, filed on Feb. 16, 2021, provisional application No. 63/147,281, filed on Feb. 9, 2021.

(51) Int. Cl.
*A61F 2/26* (2006.01)
*A61F 2/48* (2006.01)

(52) U.S. Cl.
CPC ............... *A61F 2/26* (2013.01); *A61F 2/484* (2021.08)

(58) Field of Classification Search
CPC .................................. A61F 2/26; A61F 2/484
See application file for complete search history.

(56) References Cited

U.S. PATENT DOCUMENTS

| | | | |
|---|---|---|---|
| 4,342,308 A | 8/1982 | Trick | |
| 4,550,719 A * | 11/1985 | Finney | A61F 2/26 600/40 |
| 4,602,621 A | 7/1986 | Hakky | |
| 4,682,589 A | 7/1987 | Finney | |
| 4,917,110 A | 4/1990 | Trick | |
| 8,147,400 B1 | 4/2012 | Daniel | |
| 8,348,826 B2 | 1/2013 | Gomez-Llorens | |
| 11,051,923 B2 | 7/2021 | Newman et al. | |
| 2011/0201880 A1* | 8/2011 | Fogarty | A61F 2/26 600/40 |
| 2012/0184806 A1 | 7/2012 | Daniel | |
| 2012/0184807 A1 | 7/2012 | Daniel | |
| 2016/0081802 A1* | 3/2016 | Little | A61F 2/26 600/40 |

FOREIGN PATENT DOCUMENTS

| | | |
|---|---|---|
| WO | 2012007009 A1 | 1/2012 |
| WO | 2013020555 A2 | 2/2013 |

* cited by examiner

*Primary Examiner* — Samuel G Gilbert
(74) *Attorney, Agent, or Firm* — Coloplast Corp., Coloplast A/S; Nick Baumann

(57) ABSTRACT

A pump is connected between penile cylinder(s) and a reservoir of a prosthesis. A squeezing pressure applied to the penile cylinder moves a first liquid volume out of the cylinder and into a first chamber of the pump, which displaces a piston inside of the pump. Displacement of the piston creates a vacuum space (a second chamber) between the piston and the housing of the pump, and a second liquid volume is drawn out of the reservoir and into the vacuum space. A return spring pushes the piston back to its starting position, which pushes both the first liquid volume and the second liquid volume out of the pump and into the penile cylinders.

18 Claims, 13 Drawing Sheets

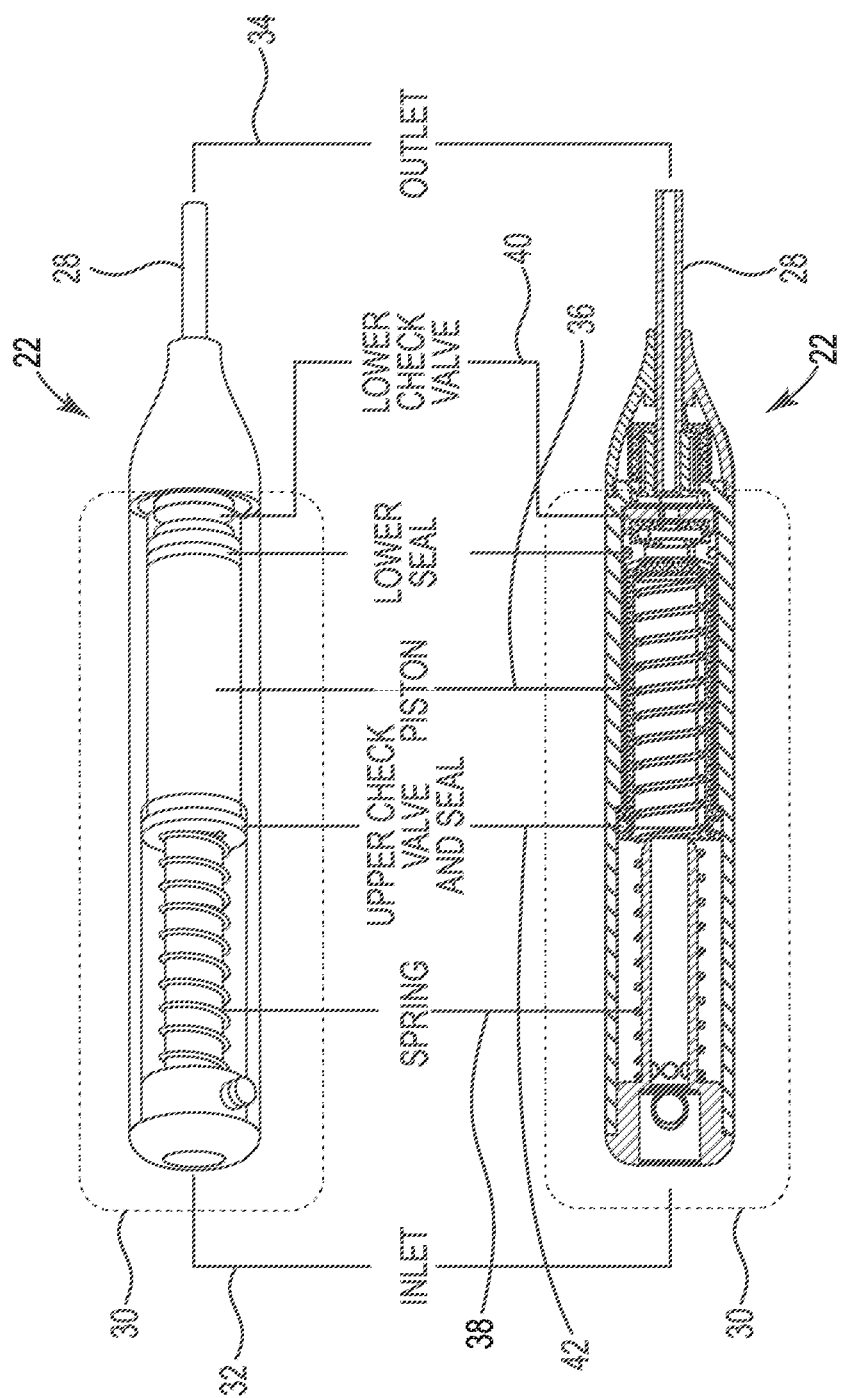

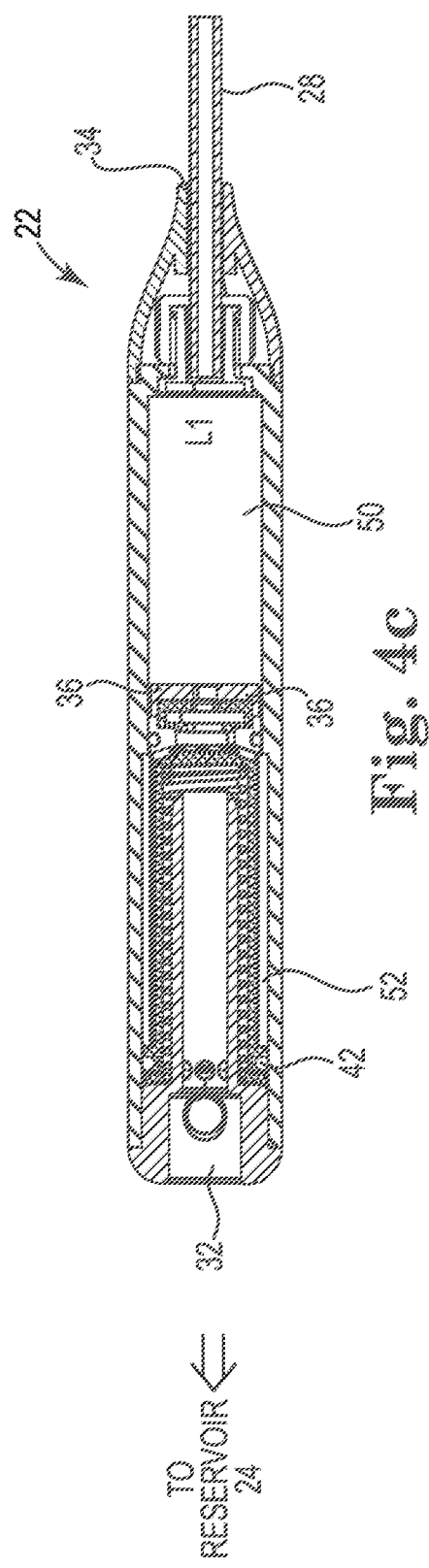
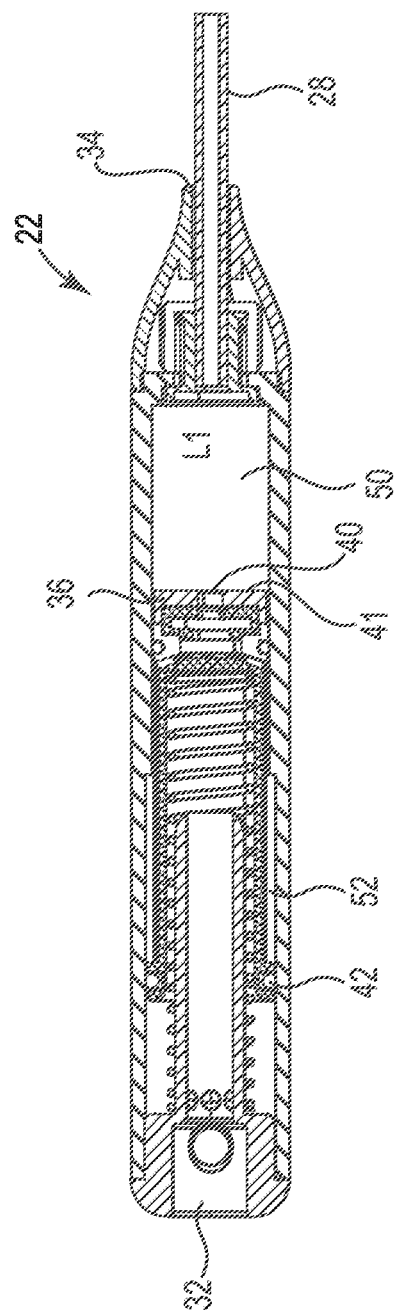

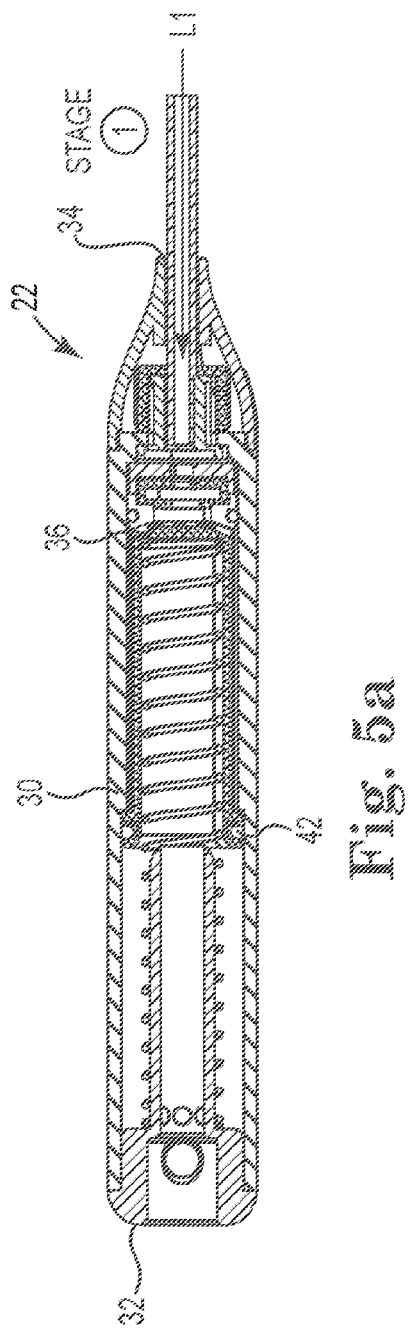
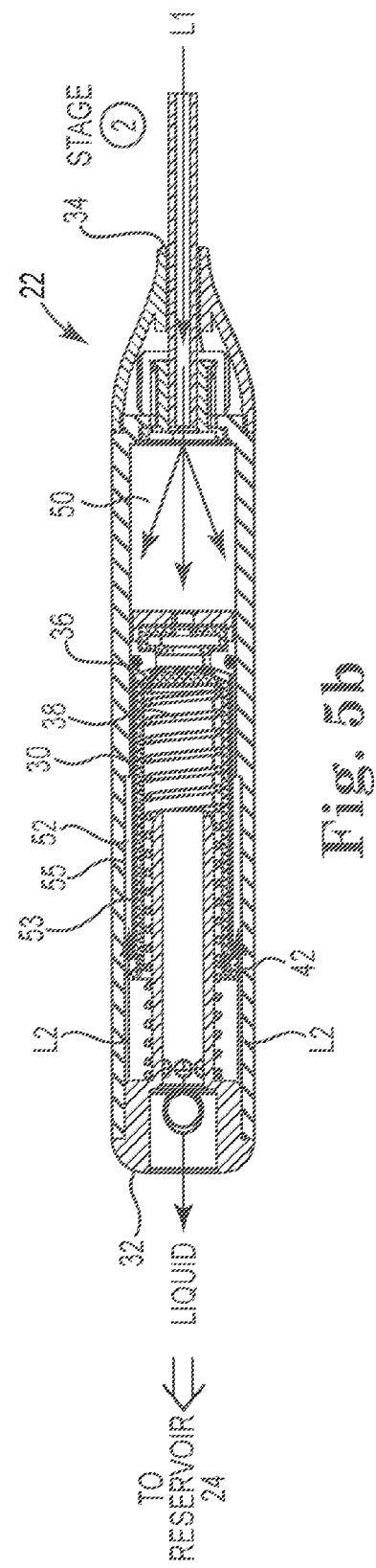

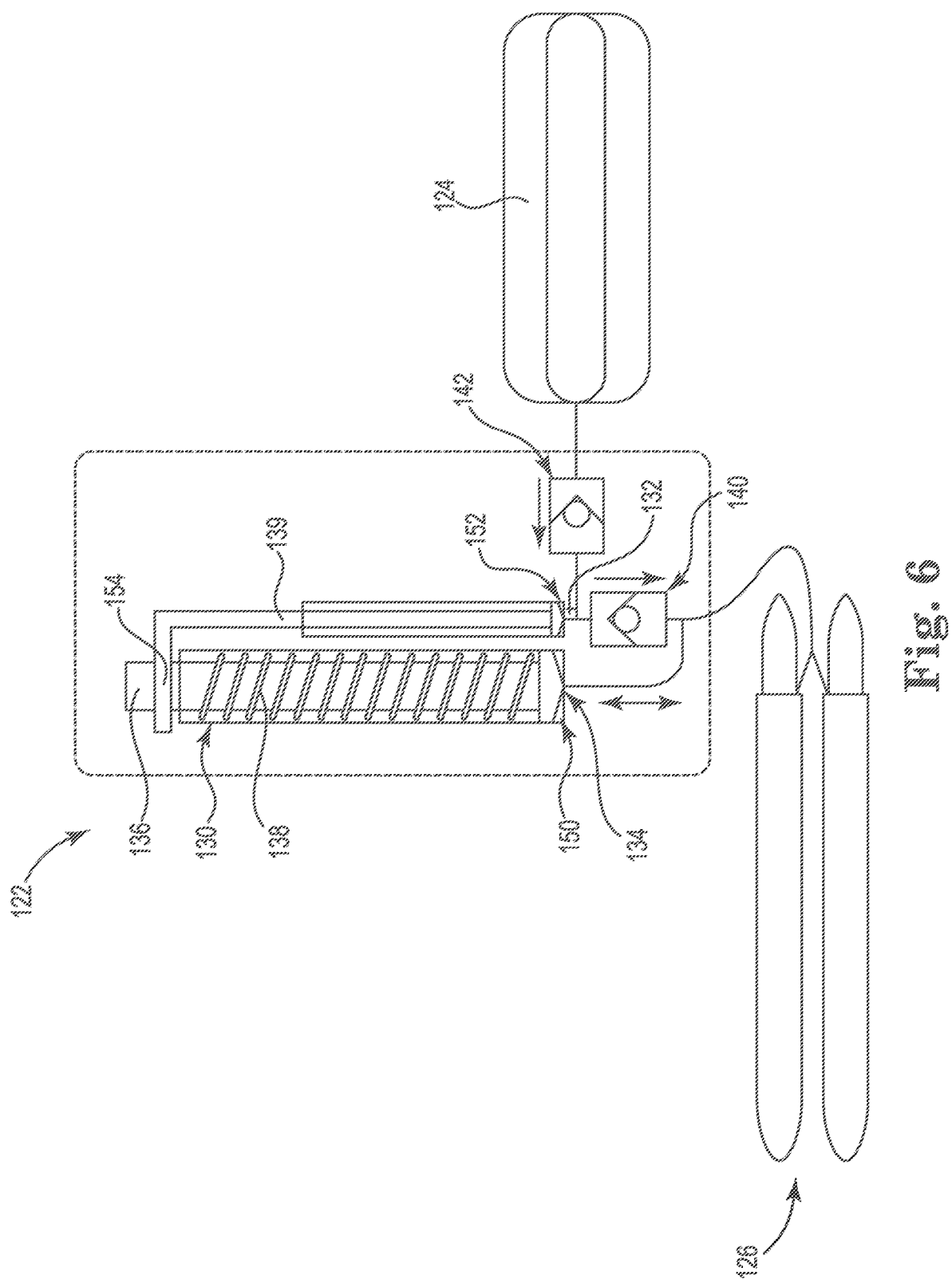

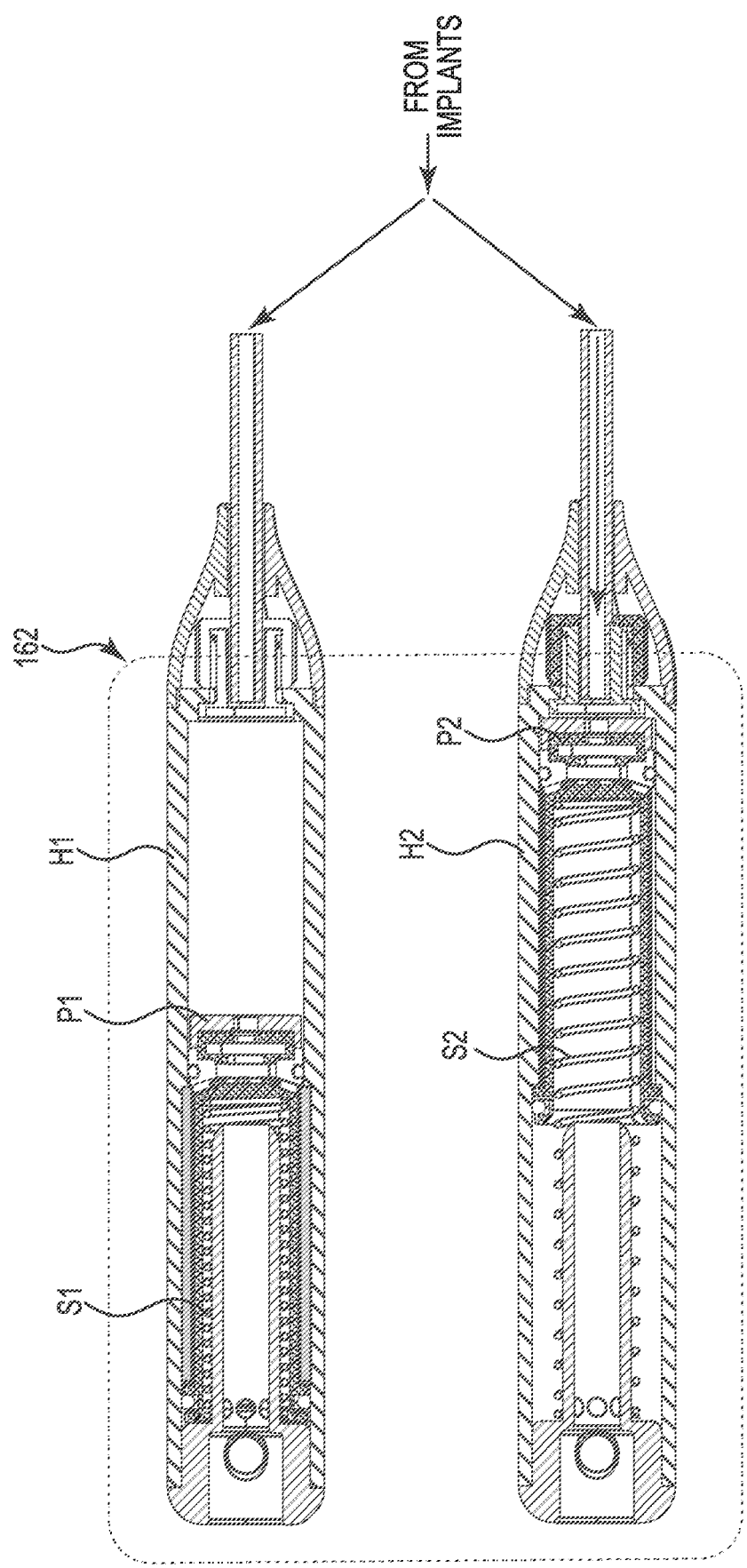

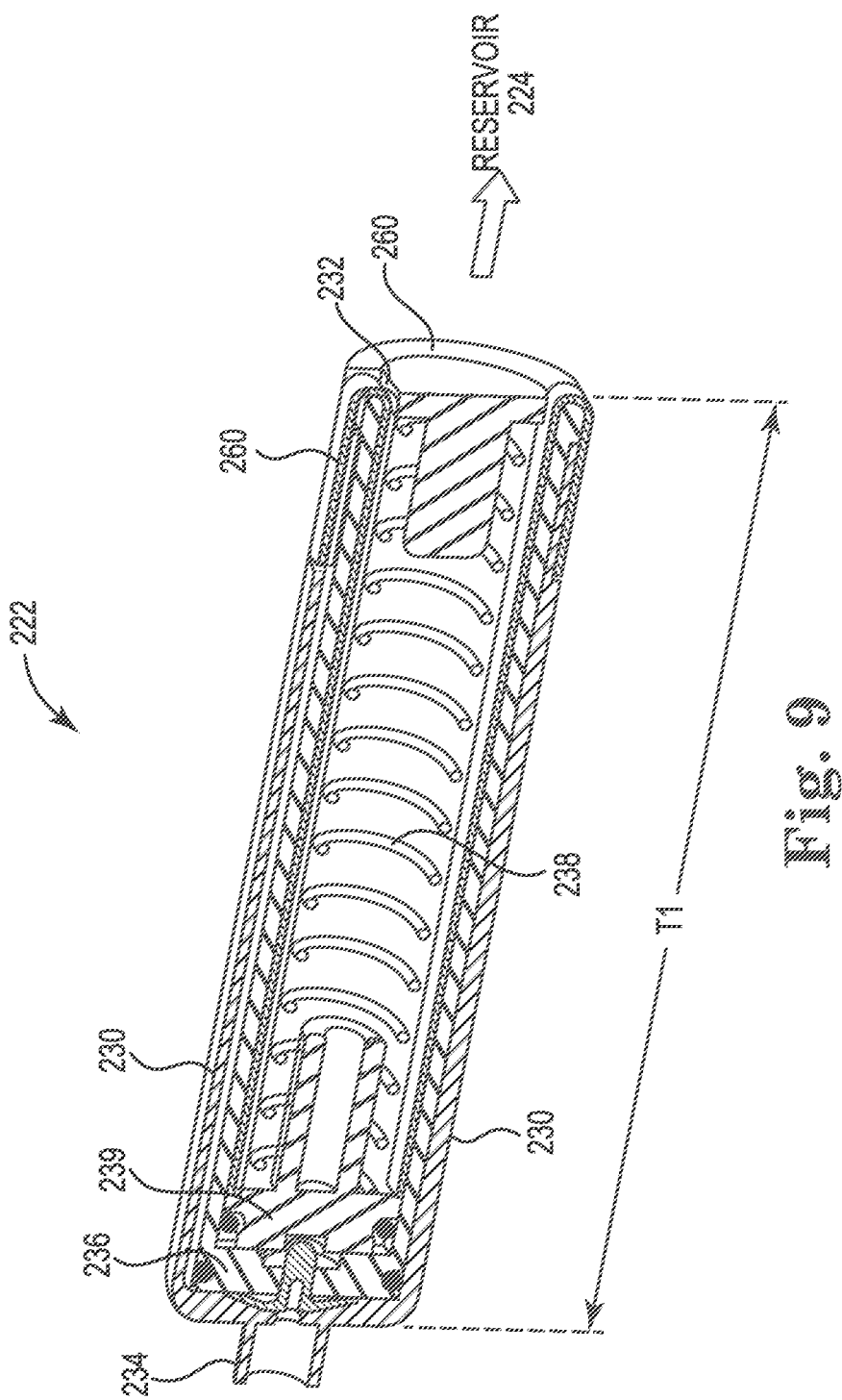

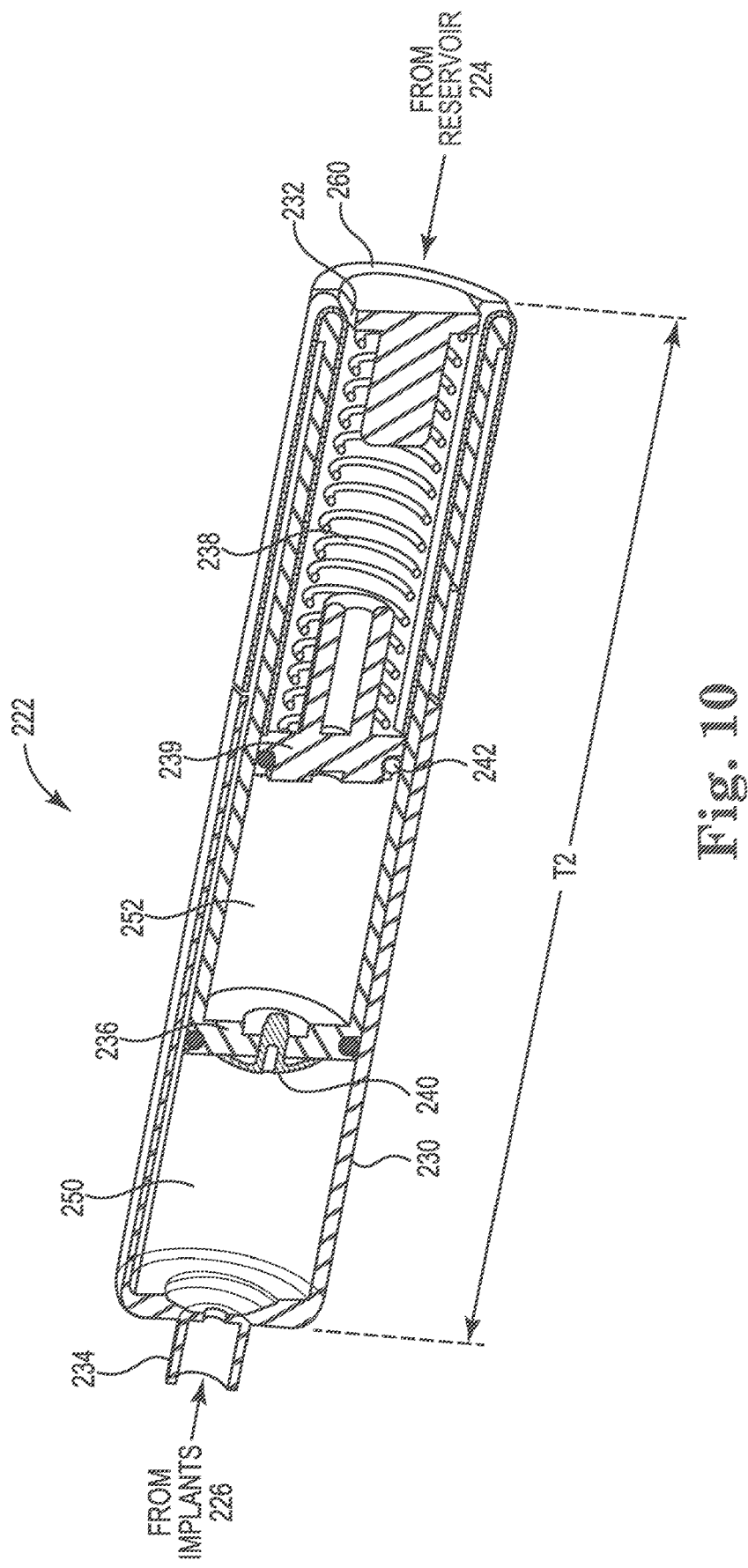

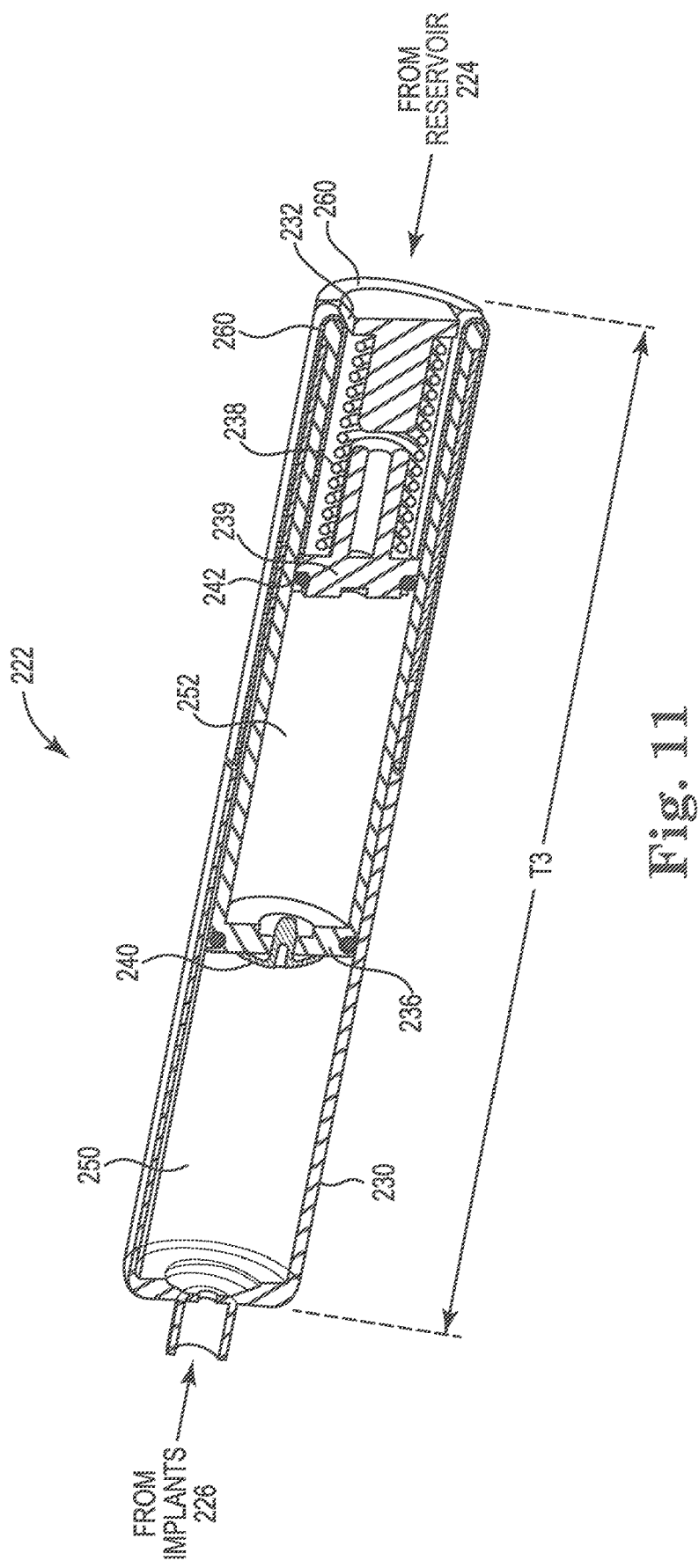

PUMP HAVING A VOLUME AMPLIFICATION MECHANISM FOR AN INFLATABLE PENILE PROSTHESIS

BACKGROUND

Inflatable penile prosthetics have proven useful in treating erectile dysfunction. The typical inflatable penile prosthetic has an implant in the penis, a reservoir implanted in the abdomen, and a pump implanted in the scrotum to move liquid out from the reservoir and into the implant in the penis.

Improvements to inflatable penile prosthetics would be welcomed by both patients and surgeons.

SUMMARY

A tidal pump is described that allows for volume amplification when inflating an inflatable penile prosthesis. The tidal pump is a named architecture for this form of pump for an inflatable penile prosthesis where the inflatable portion of the penile implant is utilized to actuate the pump with an initial volume of liquid, and the pump responds by transferring a second volume of liquid along with the initial volume of liquid back to the inflatable implant. The pump is generally located between an inflatable implant and a reservoir, with an outlet of the pump communicating with the implant and an inlet of the pump communicating with the reservoir. During use of the system, a squeezing action applied to the inflatable implant by squeezing the penis pushes (or pressurizes) a first volume of liquid out of the implant and into an outlet of the pump, which moves or displaces a piston inside of the pump and also displaces an upper check valve in the pump. Movement of the piston draws a second volume of liquid out from a reservoir through the upper check valve and into an inlet of the pump. The pump now contains the first volume of liquid that entered the pump through the outlet and the second volume of liquid that entered the pump through the inlet. The eventual return of the piston pushes the first volume and the second volume of liquid out of the outlet of the pump and into to the inflatable implant. Advantageously, the squeeze of the implant displacing the first volume of liquid results in both the first volume of liquid plus the second volume of liquid entering back into the implant, which could allow a user to inflate the implant with fewer squeezes of the disclosed tidal pump as compared to a traditional pump usually implanted in the scrotum. Thus, the tidal pump produces a net gain of liquid (i.e., the second volume of liquid) delivered to the inflatable implant with every squeeze of the implant, as one example. For these reasons, the tidal pump is referred to as a volume amplification mechanism when used with a penile implant.

The tidal pump is connected between penile cylinder(s) of the implant and a reservoir of the prosthesis, for example with tubing, or kink-resistance reinforced (reinforced with metal or nylon) polymer tubing. A squeezing pressure applied to the penile cylinder through the penis moves a first liquid volume out of the cylinder and into a first chamber of the tidal pump, which displaces a piston inside of the tidal pump and opens an upper check valve. Displacement of the piston creates a vacuum space (a second chamber or a suction chamber) between the piston and the housing of the tidal pump, and a second liquid volume is drawn out of the reservoir, through the upper check valve, and into the suction chamber. A return spring pushes the piston back to its starting position, which pushes both the first liquid volume and the second liquid volume out of the tidal pump and into the penile cylinders. Thus, the volume gained in the penile cylinder with use of the tidal pump is about equal to the volume of the second chamber. Repeated squeezing of the penile cylinder leads to an accumulation of liquid in the cylinder, which inflates the cylinder and results in an erection when the prosthesis is implanted.

The above description will allow a person of skill in the art to understand that a single squeeze of the penile cylinder results in a subsequent return of liquid back into the cylinder that is larger than the amount of liquid initially displaced out of the cylinder. If the first chamber has the same size as the second chamber (the suction chamber), then the liquid volume moved from the tidal pump back into the cylinder is amplified by a factor of 2 (e.g., the volume in the first chamber and the volume from the second chamber from the tidal pump is returned to the cylinder in exchange for the volume in the first chamber that initially came from the cylinder). Thus, each squeeze of the cylinder in this example results in a 2-for-1 amplification of fluid volume back to the cylinder (a volume gain). Other ratios of the size of the first chamber to the second chamber are possible, so that the tidal pump may be configured or designed to adjust the liquid volume gain based upon a selected design of the geometries of the first and second chambers in the tidal pump. A typical volume gain for the tidal pump is between the range from 0.5 to 1.0 cc.

The beneficial volume gain described above is balanced by the role of the spring constant for the return spring. The pressure of the squeeze to the implant cylinder applies a force to the face of the piston. The return spring will compress in response to this force (this is Hooke's law: $F=k*displacement$, where k is the spring constant). If a user applies a forceful squeeze to the cylinder, then the spring of a given constant k will displace according to Hooke's law and return a proportionally large volume of liquid gain. If, however, the user applies a weak or gentle squeeze to the cylinder, the same spring will not displace the same amount, thus returning a small liquid gain. Consequently, the beneficial liquid gain achieved by a selected geometry of the tidal pump chambers is balanced by the spring constant of the return spring. In other words, the trade-off is generally between designing a tidal pump that performs with a few high-pressure cylinder squeezes providing repeated large volume gains (for people with strong hands), or many low-pressure cylinder squeezes providing repeated smaller volume gains (for people with limited dexterity or strength in their hands).

In any regard, the tidal pump described in this application allows for a range of volume gains based on a selected geometry between the two chambers and the selected spring constant k.

Embodiments of the tidal pumps may use either simple constant K springs, or rising rate springs depending on the desired characteristics, equally alternative embodiments can be conceived using pneumatic or other gas springs.

One embodiment of an inflatable penile prosthesis comprising a tidal pump coupled in fluidic communication between a reservoir and a penile implant comprises: a housing having an inlet end attachable to the reservoir and an outlet end attachable to the penile implant; a first piston biased within the housing by a return spring such that a displacement of the first piston away from the outlet end of the housing opens a first chamber communicating with the penile implant and a second chamber communicating with the reservoir; a first check valve positioned between the first chamber and the outlet end; and a second check valve positioned between the second chamber and the inlet end; wherein a first volume of liquid moved from the penile implant into the first chamber displaces the first piston to form a suction within the second chamber that draws a second volume of liquid from the reservoir and into the second chamber; wherein a return of the first piston toward the outlet end of the housing moves the first volume of liquid and the second volume of liquid into the penile implant.

One embodiment of an inflatable penile prosthesis having a pump coupled in fluidic communication between a reservoir and a penile implant provides a pump comprising:

a housing having an inlet end communicating with the reservoir and an outlet end attachable to the penile implant;

a first piston biased within the housing by a return spring such that a displacement of the first piston away from the outlet end of the housing forms a first chamber communicating with the penile implant and forms a second chamber communicating with the reservoir;

a first check valve positioned between the first chamber and the outlet end; and a second check valve positioned between the second chamber and the inlet end;

configured such that:
  a) moving a first volume of liquid from the penile implant displaces the first piston and transfers the first volume of liquid into the first chamber,
  b) displacement of the first piston creates a suction within the second chamber that draws a second volume of liquid from the reservoir and into the second chamber, and
  c) a return of the first piston toward the outlet end of the housing moves the first volume of liquid and the second volume of liquid into the penile implant.

The penile implant described in this application would be implanted within the penis and the pump would be implanted in the body but outside of the penis, for example within the abdomen or within the scrotum. The pump communicates with a reservoir. One embodiment locates the pump inside of a reservoir and both the pump and the reservoir are implanted in the body. The reservoir and the pump could be separate units and connected by suitable tubing. Benefits and advantages of the tidal pump include inflation of the implanted penile implant by the user through the action of squeezing of the penis. Each squeeze applied to the penis by the user sends liquid into the pump and results in more liquid (e.g., a volume gain) returned from the pump back to the implant in the penis, and this volume gain accumulates with subsequent squeezes to inflate the penile implant thus treating erectile dysfunction. The advantages include: a more natural approach to achieving an erection; the option of removing the pump from inside the scrotum, as some users occasionally find it challenging to squeeze a pump bulb when it is located within the scrotum; and a potentially smaller pump footprint, which allows for increased patient comfort.

Benefits and advantages of the tidal pump include a smaller plan form for implantation in a pump that moves liquid into a penile implant through the squeezing of the implant. Since the penile portion of the implant is in an implant cylinder within the penis, the user may easily access the implant cylinder to initiate the squeezing that begins the liquid pumping process.

Other advantages of the tidal pump include that the pump can be inserted into the reservoir, thus the system of parts represents a two-piece implant of 1) a pump inside of a reservoir, and 2) the penile implants coupled to the pump. This architecture obviates a three-piece system having a penile implant coupled to both a body-implanted reservoir and a pump, where the pump has a pump body and a pump bulb that are usually implanted into a scrotum of a patient. Other advantages of the tidal pump include fewer tube-to-component connections to be made by the surgeon during implantation.

The check valves described in this application are configured as one-way check valves that allow liquid to move through the check valve in one direction and prevent the liquid from moving through the check valve in the opposite direction. Other forms of check valves are envisioned to be acceptable.

An aspect of this embodiment includes, wherein the first chamber is located between a face of the piston and the outlet end of the housing and the second chamber is located between a side wall of the piston and an internal wall of the housing.

An aspect of this embodiment includes, wherein the first check valve is formed in the face of the piston, and the second check valve seals the trailing end of the piston relative to the internal wall of the housing.

An aspect of this embodiment includes, wherein the first chamber is co-axial with the second chamber.

An aspect of this embodiment further comprises: a second piston within the housing, where the first piston and the second piston are oriented side-by-side and the first chamber is separated away from the second chamber.

An aspect of this embodiment includes, wherein the first check valve is located between the first piston and the second piston, and the second check valve is located between the reservoir and the housing.

An aspect of this embodiment includes, wherein the first chamber is co-axial with the second chamber, and further comprising: a second piston biased within the housing, where the first piston and the second piston are each movable within the housing and the second piston is nested inside of the first piston.

An aspect of this embodiment includes, wherein the second piston is coupled with the first piston by a pulley strap.

A method of inflating the penile implant of this embodiment includes:

providing the inflatable penile prosthesis and configuring the inflatable penile prosthesis to operate such that:
  1) squeezing the penile implant increases a pressure of liquid in the penile implant thus moving a first volume of the liquid from the penile implant into the first chamber;
  2) displacing the first piston away from the outlet end of the housing with the first volume of liquid and forming a suction in the second chamber;
  3) drawing a second volume of liquid out of the reservoir and into the second chamber; and
  4) biasing the first piston toward the outlet end of the housing with the return spring and moving first volume of liquid and the second volume of liquid into the penile implant.

One embodiment of an inflatable penile prosthesis comprising a tidal pump coupled in fluidic communication between a reservoir and a penile implant comprises: a housing having an inlet end attachable to the reservoir and an outlet end attachable to the penile implant, with the housing forming a first chamber adapted for fluid communication with the penile implant; a piston retained in the housing, with a face of the piston disposed within the chamber and a portion of the piston spaced a distance away an internal wall of the housing to form a suction chamber adapted for fluid communication with the reservoir; a return spring coupled between the piston and the housing; an upper check valve coupled to the piston, with the piston sealed relative to the suction chamber; and a lower check valve formed on the outlet end of the housing.

One embodiment of an inflatable penile prosthesis comprising a tidal pump coupled in fluidic communication between a reservoir and a penile implant comprises: a housing having an external wall, an internal wall, an inlet end attachable to the reservoir, and an outlet end attachable to the penile implant; a piston inserted in the housing, with the piston having a face end oriented toward the outlet end of the housing and a trailing end oriented toward the inlet end of the housing; a return spring connected between the trailing end of the piston and the inlet end of the housing; a first fluid chamber located between the face end of the piston and the outlet end of the housing; and a second fluid chamber located between the piston and the internal wall of the housing.

Another embodiment of an inflatable penile prosthesis comprising a pump coupled in fluidic communication between a reservoir and a penile implant includes a pump comprising:
 a housing having an inlet end adapted to communicate with the reservoir and an outlet end adapted to communicate with the penile implant;
 a first piston retained in and biased relative to the housing, where displacement of the first piston within the housing forms a first chamber that communicates with the penile implant and a suction chamber that communicates with the reservoir;
 a first check valve disposed between the first chamber and the penile implant; and
 a second check valve disposed between the suction chamber and the reservoir;
 wherein movement of an implant liquid out of the penile implant is adapted to:
  a) displace the first piston within the housing to allow the implant liquid to enter the first chamber, and
  b) create suction within the suction chamber to draw a reservoir liquid from the reservoir into the suction chamber;
 wherein a return of the first piston within the housing pushes the implant liquid though the first check valve and pushes the reservoir liquid through the second check valve, with both of the implant liquid and the reservoir liquid moving into the penile implant.

An aspect of this embodiment includes, wherein the first chamber is located between a face of the first piston and the outlet end of the housing, and the suction chamber is located between a side wall of the first piston and an internal wall of the housing. This structure advantageously provides a compact pump with co-axial chambers.

An aspect of this embodiment further comprises:
 a second piston within the housing, where the first piston and the second piston are oriented side-by-side;
 wherein the first chamber is located between a face of the first piston and the outlet end of the housing and the suction chamber is located between a face of the second piston and the inlet end of the housing. This structure advantageously allows selection of a broad range of ratios between the size of the first chamber and the size of the second (or suction) chamber, which relates to the ratio of volume amplification described above.

An aspect of this embodiment includes, wherein the first check valve is located between the first piston and the second piston, and the second check valve is located between the reservoir and the housing.

An aspect of this embodiment includes, wherein the first chamber is co-axial with the suction chamber, and further comprising:
 a second piston biased within the housing, where the first piston and the second piston are each movable within the housing, with the second piston co-axial with the first piston, and the second piston is coupled with the first piston by a pulley strap.

Another embodiment of an inflatable penile prosthesis comprising a pump coupled in fluidic communication between a reservoir and a penile implant provides a pump comprising:
 a housing having an external wall, an internal wall, an inlet end attachable to the reservoir, and an outlet end attachable to the penile implant;
 a piston inserted in the housing, with the piston having a face end oriented toward the outlet end of the housing and a trailing end oriented toward the inlet end of the housing;
 a return spring connected between the trailing end of the piston and the inlet end of the housing;
 a first fluid chamber located between the face end of the piston and the outlet end of the housing; and
 a second fluid chamber located between the piston and the internal wall of the housing.

An aspect of this embodiment includes a first check valve disposed between the first fluid chamber and the penile implant.

Another aspect of this embodiment includes a second check valve disposed between the second fluid chamber and the reservoir.

BRIEF DESCRIPTION OF THE DRAWINGS

The accompanying drawings are included to provide a further understanding of embodiments and are incorporated in and constitute a part of this specification. The drawings illustrate embodiments and together with the description explain principles of embodiments. Other embodiments and advantages of embodiments will be readily appreciated as they become better understood by reference to the following detailed description. The elements of the drawings are not necessarily to scale relative to each other. Like reference numerals designate corresponding similar parts.

FIG. 3 is a side view and a cross-sectional view of one embodiment of a tidal pump.

FIG. 4a through FIG. 4d are a series of cross-sectional views of the operation of the tidal pump.

FIG. 5a through FIG. 5d are a series of cross-sectional views showing fluid movement during the operation of the tidal pump.

FIG. 6 is a front view of one embodiment of a tidal pump including a piston housing separated from a fluid chamber housing.

FIG. 7 is a cross-sectional view of one embodiment of a tidal pump utilizing two housings and two different springs each having a different spring constant.

FIG. 9 is a view of the tidal pump of FIG. 8 in a closed initial state.

FIG. 10 is a view of the tidal pump of FIG. 8 with a first chamber and a second chamber during a pumping state.

FIG. 11 is a view of the tidal pump of FIG. 8 with the first chamber and the second chamber full of liquid during a pumping state prior to inflation of a penile cylinder.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used regarding the orientation of the Figure(s) being described. Because components of embodiments can be positioned in several different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other, unless specifically noted otherwise.

The term "proximal" in this application means that part that is situated next to or near the point of attachment or origin or a central point; for example, as located toward a center of the human body. The portion of an implant that is closest to a center of a patient's body is the proximal portion of the implant. Also, for a surgical tool having a handle and a working head, the handle held by the surgeon is a proximal portion of the tool.

The term "distal" in this application means that part that is situated away from the point of attachment or origin or the central point; for example, as located away from the center of the human body. The working head of the surgical tool is distal relative to the proximal handle.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12-inch ruler has a center at 6 inches, a first end at zero inches and a second, opposite end at 12 inches, a first end portion adjacent to the first end and a second end portion adjacent to the second end.

FIGS. 1-5 illustrate one embodiment of a tidal pump 22 that represents a refinement beyond the initial and bulkier two-piston prototype of a tidal pump 122 illustrated in FIG. 6. FIGS. 8-11 illustrate an embodiment of a tidal pump 222 offering a similar performance to the tidal pump 22 of FIGS. 1-5, but in a conformation that includes a telescoping piston. The performance of the embodiments 22, 122, and 222 can be configured to be similar one to another by modifying the spring constant and the area ratios of the two chambers.

Figure 1:
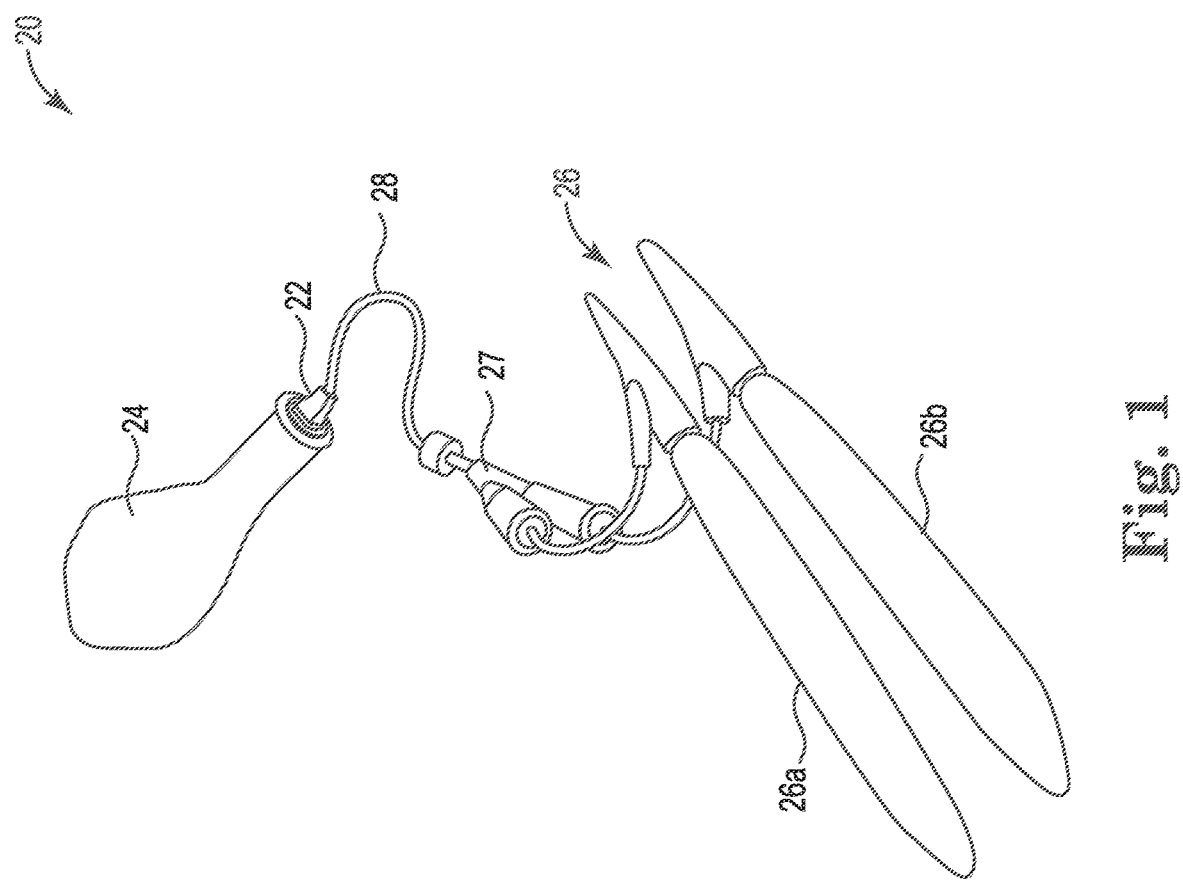
FIG. 1 is a perspective view of one embodiment of a penile prosthesis including a tidal pump coupled in fluidic communication between a reservoir and a penile implant.

FIG. 1 is a perspective view of one embodiment of a penile prosthesis 20 including a tidal pump 22 coupled in fluidic communication between a reservoir 24 and a pair 26 of penile implants via tubing 28. Each penile implant 26a, 26b of the pair 26 of penile implants is attachable to a connector 27 that combines the separate flows paths from the implants 26a, 26b into a single flow path connected with the tubing 28.

Figure 2:
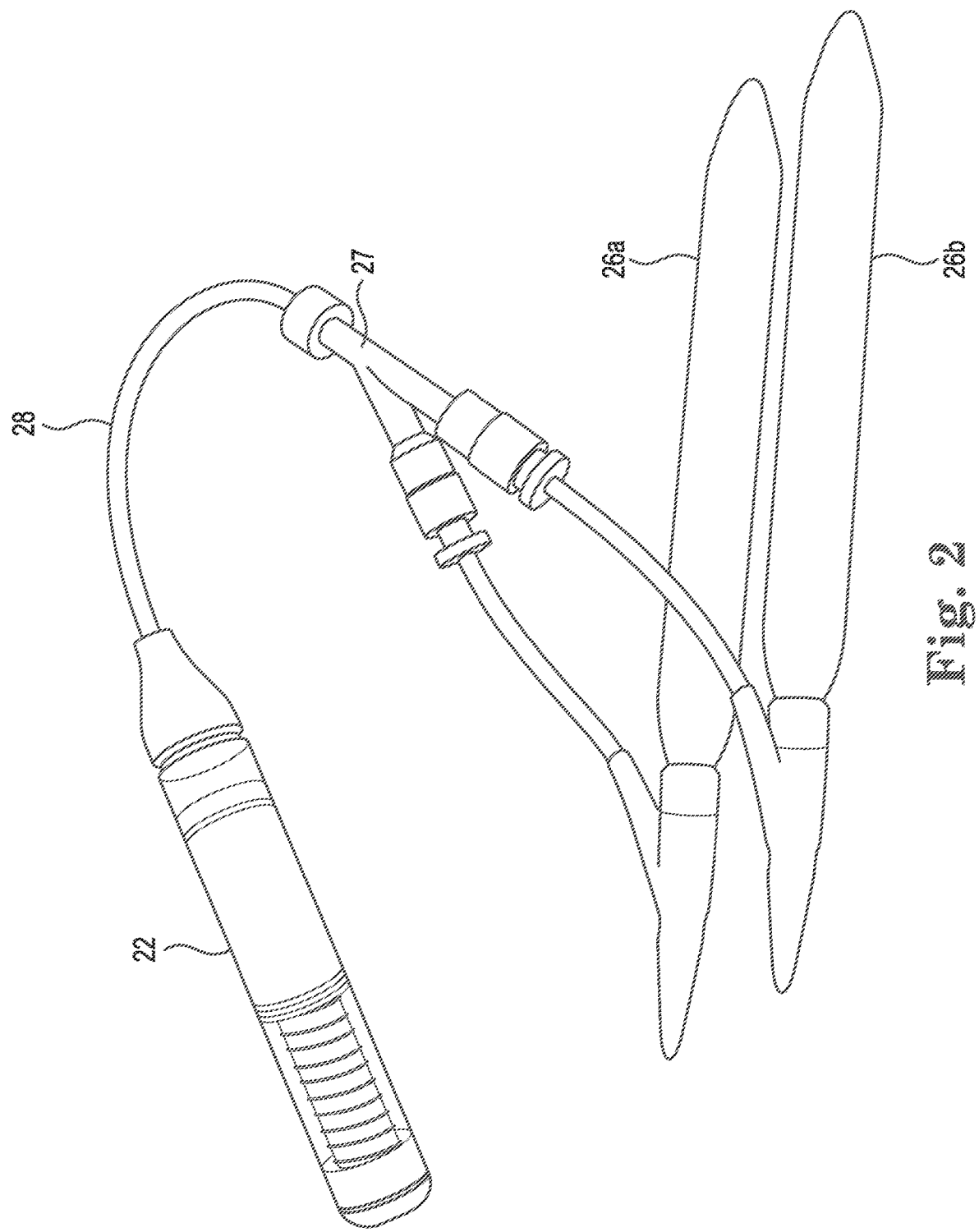
FIG. 2 is a perspective view of one embodiment of a tidal pump coupled in fluidic communication with a penile implant.

FIG. 2 is a perspective view of the tidal pump 22 withdrawn out of the reservoir 24 while connected to the penile implants 26a, 26b via tubing 28.

FIG. 3 is a schematic view illustrating a naming convention of the components of the tidal pump 22, where the schematic view shows a perspective view imposed over a cross-sectional view for a better understanding of the naming convention.

Figure 4A:
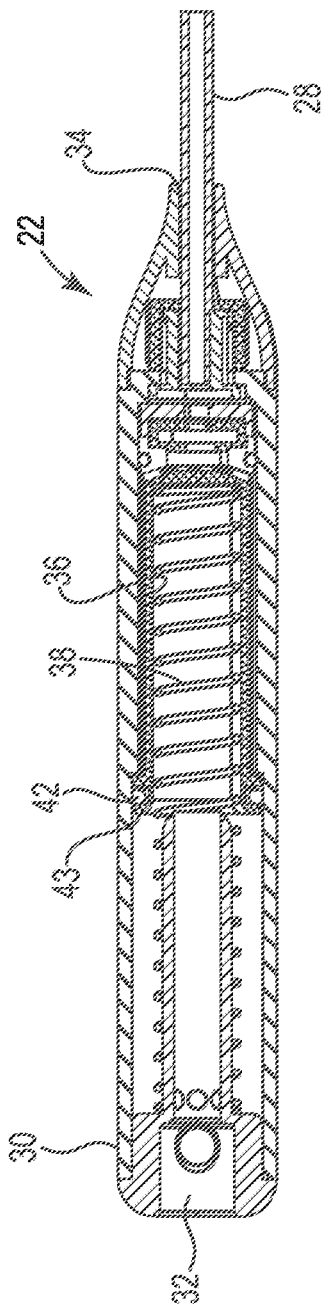
Figure 4B:
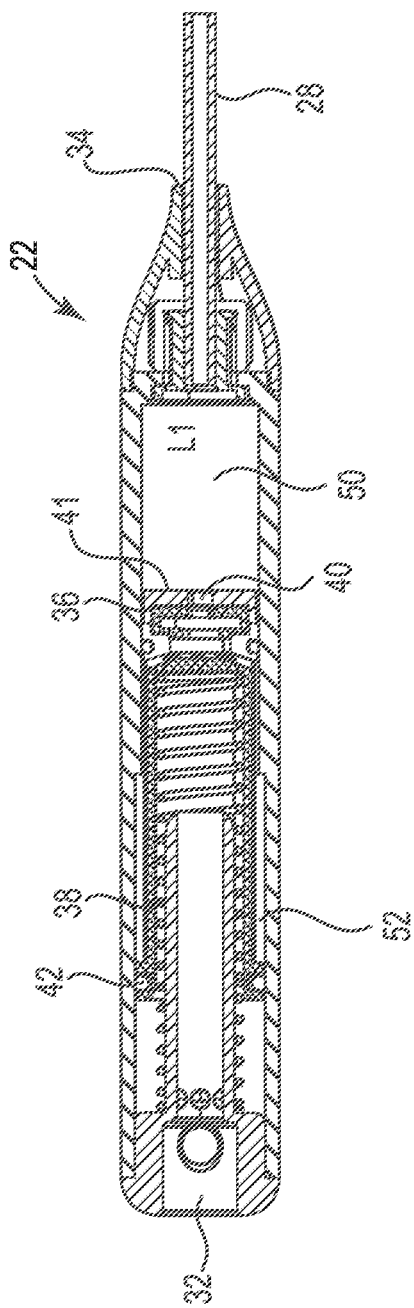

FIG. 4a through FIG. 4d are a series of four cross-sectional views (FIG. 4 (*a*), (*b*), (*c*), and (*d*)) of the tidal pump 22 at different stages of operation.

Figure 5C:
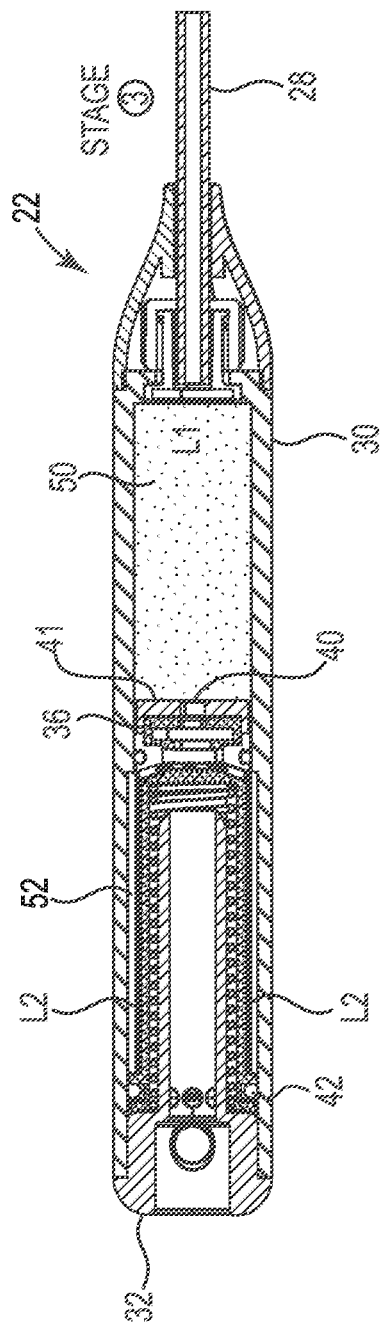

The tidal pump 22 (or pump 22) includes a housing 30 having an inlet end 32 attachable to the reservoir 24 (FIG. 1) and an outlet end 34 attachable to the penile implants 26a, 26b (FIG. 1) by the tubing 28. A first piston 36 (or piston 36) is biased within the housing 30 by a return spring 38. With reference to FIG. 5b and FIG. 5c, a first check valve 40 or lower check valve 40 is formed in the face 41 of the piston 36 adjacent to the outlet end 34 and a second check valve 42 or upper check valve 42 is positioned at a trailing end 43 of the piston 36 adjacent to the inlet end 32 of the housing 30. The first check valve 40 prevents the liquid L1 drawn from the implants and into the first chamber 50 from moving past the piston 36 toward the second chamber 52. The second check valve 42 prevents the liquid L2 drawn from the reservoir and into the second chamber 52 from flowing back to the reservoir. In one embodiment, the first valve 40 and the second valve 42 operate as one-way check valves.

FIG. 4(*a*) is a cross-sectional view showing the spring 38 extended (not displaced) within the housing 30 and the piston 36 is closed and adjacent to the outlet end 34.

FIG. 4(*b*) shows a first volume of liquid L1 has been moved from the penile implants 26a, 26b, resulting in a displacement of the piston 36 and compression of the spring 38. The displacement of the piston 36 away from the outlet end 34 of the housing 30 forms a first chamber 50 communicating with the penile implant 26. The first volume of the liquid L enters the first chamber 50. The displacement of the piston 36 forms a second chamber 52 between an exterior wall of the piston 36 and an interior wall of the housing 30. The void that is created in the second chamber 52 by the displacement of the piston 36 forms a suction within the second chamber 52 that draws a second volume of liquid L2 from the reservoir 24, through the second check valve 42, and into the second chamber 52.

FIG. 4(*c*) shows an embodiment where the spring 38 is compressed and the volumes in the first chamber 50 and the second chamber 52 are as large as possible for a given spring constant of the spring 38 and the relative sizes of chamber 50 and chamber 52, or as large as possible given the limit on the range of displacement for the piston 36.

FIG. 4(*d*) shows partial movement of the spring 38 back toward the outlet end 34. When the piston 36 is moved back toward the outlet end 34 of the housing 30, the second check valve 42 prevents the second volume of liquid L2 from moving toward the reservoir 24 and both the first volume of liquid L1 and the second volume of liquid L2 are delivered into the penile implant 26.

One suitable spring 38 includes a spring with a 1.4 lb/in spring rate, 4 inches in total length, and with a pre-compression length of 1.35 inches when in the 'at rest' position shown in FIG. 3 and in FIG. 5a (Stage 1).

The pump 22 has a housing diameter of approximately 16 mm (1.6 cm) and length in a range from about 6 to 12 cm.

The cross-sectional shape is circular, but other cross-sectional shapes are also acceptable.

FIG. 5a through FIG. 5d are a series of four cross-sectional views of the tidal pump 22 during one cycle of a volume amplification of the liquid used to inflate the penile prosthesis. The following description is made with reference to the identifiers from FIG. 1 to FIG. 4d.

FIG. 5a Stage 1 illustrates a view after a squeezing of the cylinder of the penile implants 26a, 26b, which moves a first volume of liquid L1 out of the cylinder of the penile implants 26a, 26b, though the outlet end 34 of the housing 30, and into the first chamber 50 located between the outlet end 34 and the face 41 of the piston 36. The movement of the first volume of liquid L1 displaces the piston 36 rearward in the housing 30 toward the inlet end 32.

FIG. 5b Stage 2 illustrates that the displacement of the piston 36 toward the inlet end 32 of the housing 30 has the potential to eject some liquid (arrow pointing to the left) that may have gathered within the recesses of the spring 38 and piston 36 components back toward the reservoir 24 through the inlet end 32. In addition, the displacement of the piston 36 toward the inlet end 32 of the housing 30 forms a void or open space between an exterior wall of the piston 36 and an interior wall of the housing 30. The void or space is the second chamber 52, and in this embodiment, the second chamber 52 is located between a sidewall 53 of the piston 36 and an internal wall 55 of the housing 30. The formation of the void in opening the second chamber 52 creates a suction or a region of lower pressure, which draws a second volume of liquid L2 out of the reservoir 24, through the inlet end 32 of the housing 30 (shown by two arrows within the chamber 52 pointing to the right), and through the second check valve 42. The second volume of liquid L2 is retained in the second chamber 52 illustrated at Stage 3.

FIG. 5c Stage 3 illustrates the first volume of liquid retained L1 in the first chamber 50 between the outlet end 34 and the face 41 of the piston 36 and the second volume of liquid L2 retained in the second chamber 52. The first check valve 40 prevents the first volume of liquid L1 from moving past the piston 36 toward the second chamber 52. The second check valve 42 prevents the second volume of liquid L2 from moving back into the reservoir 24.

Figure 5D:
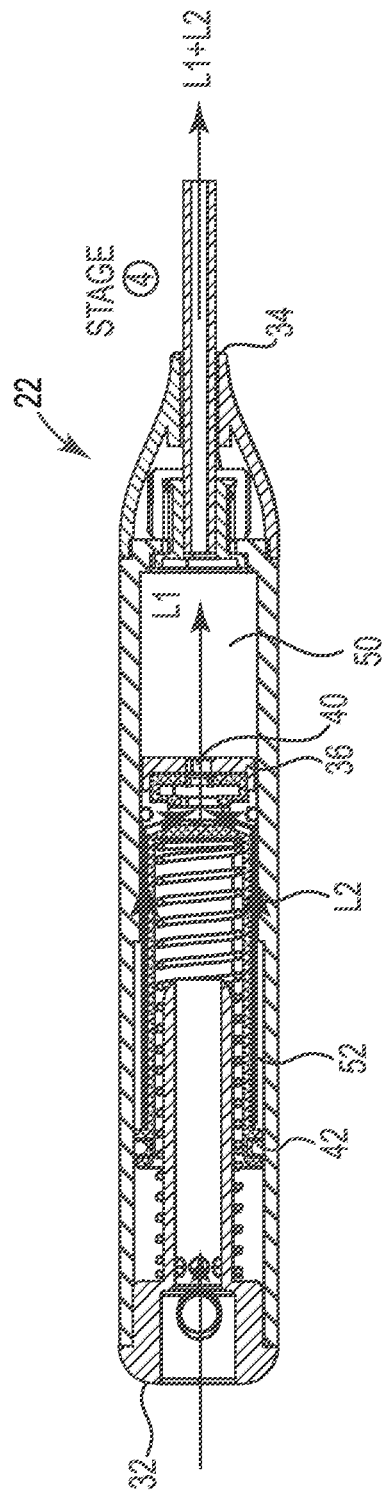

FIG. 5d Stage 4 illustrates the displacement of the piston 36 toward the outlet end 34 of the housing 30, which drives the first volume of liquid L1 and the second volume of liquid L2 through the outlet end 34 of the housing 30 and into the cylinder of the penile implants 26a, 26b. Note that in Stage 4 the second volume of liquid L2 passes "one-way" through the first check valve 40 on its path to the cylinder of the penile implants 26a, 26b.

The process described above for the exemplary four stages (FIG. 5a through FIG. 5d) is operated cyclically. Each squeeze to the cylinder of the implants 26 systematically moves the piston 36, which adds liquid to both chambers 50, 52 (liquid L1 from the implants 26 and L2 from the reservoir 24) as described above, and upon return of the piston 36 due to the bias of the return spring 38, the volume of liquid from chambers 50, 52 (L1+L2) is ejected into the cylinder of the implants 26. Thus, cyclical squeezing of the implant 26 eventually pressurizes the implant 26 to a rigidity useful for penetrative intercourse.

FIG. 6 is a front view of one embodiment of a tidal pump 122 that was reduced to practice as an example of a working tidal pump. The first prototypes of the tidal pump (for example pump 22 of FIG. 2) functioned well but could be challenging to fully inflate for those with weak hands (i.e., limited squeezing pressure) or limited dexterity. Squeezing the cylinders required a fair amount of effort, and it was also observed that the size of the hands could influence the experience of squeezing the cylinders. Hands that were larger in size seemed to have more difficulty and discomfort squeezing the cylinders, perhaps because grip strength at the extremes of the finger flexing was weaker than with fingers in a more neutral position.

Several parameters influence the performance of the tidal pumps, including the diameters of the piston 36 and its housing 30, the size and spring constant of the spring 38, and the overall stroke length of the piston 36 in the pump 22. We observed that a relatively high squeezing pressure was called for even when the implants 26 were not fully filled with saline. Analysis showed that the spring force configuration as well as the relative sizes of the primary and secondary chambers 50, 52 contributed to the difficult use. For example, when there was no system pressure in the implants 26 (i.e., the implant 26 was incompletely filled with liquid) the user was called upon to add 10 psi of squeezing pressure to get just a small amount of fluid gain (e.g., about 0.1 cc). Furthermore, at higher pressures above about 10 psi, the amount of fluid gain that could be achieved per cycle decreased. This was because the amount of available piston stroke decreased as system pressure increased, reaching a limit for the prototype system of about 15 psi. One psi is equal to 6.89 kilopascals, so a 10 psi squeeze pressure correlates to 68.9 kPa.

However, it is noted that the performance of the tidal pump 22 was successful in inflating the implant 26, resulting in additive liquid gain in the implant 26 with each squeeze of the cylinder of the implant 26. Starting at low system pressure inside of the implant 26, each squeeze of the cylinder of the implant 26 added about 1 cc of liquid, which increased the system pressure (and rigidity of the implant 26). For system pressures between zero psi and 7 psi, each squeeze of the implant 26 caused the pump 22 to return from 0.2 cc (at a system pressure of 1 psi for example) up to 1 cc (at a system pressure of 7 psi). Above the 7 psi system pressure, squeezing of the implant 26 becomes more difficult since the implant is filling with liquid. Thus, the additive liquid gain at higher system pressures of about 8 to 15 psi reduces from about 1 cc per squeeze down to 0.2 cc or less per squeeze around the 15 psi system pressure. Consequently, subsequent squeezes of the cylinder of the implant 26 added more liquid into the implant, but the subsequent squeezes called for more hand force.

FIG. 6 is a front view of one embodiment of a tidal pump 122. The tidal pump 122 represents a side-by-side architecture having a pair of separated plungers that are rigidly connected.

The tidal pump 122 includes a housing 130 having an inlet end 132 attachable to the reservoir 124 and an outlet end 134 attachable to the penile implant 126, for example by suitable tubing. A first piston 136 is biased within the housing 130 by a return spring 138 and a second piston 139 is located within the housing 130 oriented side-by-side and spaced away from the first piston 136. The housing 130 includes the container holding the first piston 136 and the container holding the second piston 139. A first check valve 140 is placed between the second chamber 152 and the penile prosthesis 126, orientated to only allow flow from the chamber 152 into the prosthesis 126. A second check valve 142 is situated between the reservoir 124 and the inlet end 132, this valve 142 is orientated to only allow flow from reservoir 124 to the chamber inlet 132. The housing 130 thus forms an enclosure for both the first piston 136 and the second piston 139, and when these pistons are displaced, they each create an open space, or a chamber 150, 152, respectively. In this embodiment, the second piston 139 does not have a return spring, since the first piston 136 is coupled or connected to the second piston 139 by a rigid brace 154.

Squeezing or pressurizing the implant cylinder 126 moves liquid into the housing 130 to displace the first piston 136. The displacement of the first piston 136 away from the outlet end of 134 the housing 130 opens the first chamber 150 communicating with the penile implant 126, and since the first piston 136 is rigidly coupled to the second piston 139 by the brace 154, the movement of the first piston 136 results in movement of the second piston 139, which opens the second chamber 152 communicating with the reservoir 124. The opening of the second chamber 152 forms a low-pressure void (or suction) in the second chamber 152, which draws a second volume of liquid out of the reservoir 124. The return spring 138 displaces the first piston 136 (and thus also the second piston 139) back toward the bottom of the stroke, which moves both of the first volume of liquid in the first chamber 150 and the second volume of liquid in the second chamber 152 into the implant cylinder 126.

The architecture of the tidal pump 122 represents a first prototype and is bulkier than the tidal pump 22. However, the tidal pump 122 shares a common architecture with the embodiments including a piston and two chambers, where a displacement of a first liquid volume out of the penile cylinder and into a first chamber displaces a piston, and the piston displacement creates suction in a second chamber to draw a second liquid volume out of the reservoir and into the second chamber. The movement of the piston back to its starting position pushes both the first liquid volume and the second liquid volume out of the tidal pump and into the penile cylinders.

FIG. 7 is a cross-sectional view of one embodiment of a tidal pump 162 utilizing two housings H1 and H2 each with a plunger P1 and P2, respectively, and two different springs S1 and S2 each having a different spring constant. This alternative architecture illustrates that multiple such plunger/housing mechanisms can be combined to allow easier compression of the implant cylinder at squeeze pressures lower than the resistance experienced by the first piston. Note that each plunger P1, P2 includes a separate spring S1, S2, so the spring constants can be tuned to achieve a range of squeeze forces and liquid displacement. The size of each individual plunger housing H1, H2 can be selected to derive desired proportions between the liquid entering from the implant cylinder that initiates the filling cycle and the liquid ejected from the second chamber (second plunger housing). Thus, while the alternative architecture of FIG. 7 has a larger format, the range of adjustability for pump performance is increased.

Figure 8:
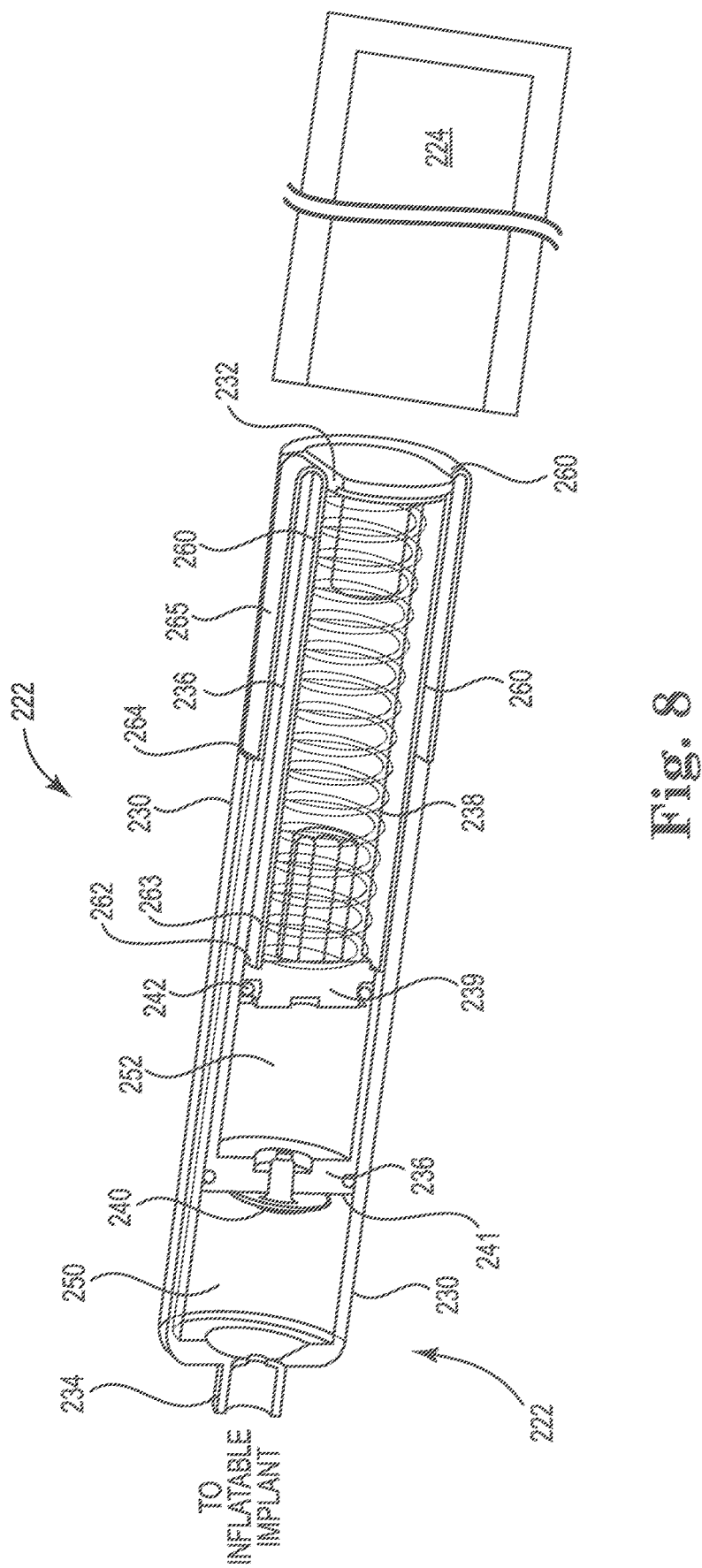
FIG. 8 is a perspective view of one embodiment of a tidal pump.

FIG. 8 is a perspective view of one embodiment of a tidal pump 222 having nested pistons 236, 239.

FIG. 9 is a view of the tidal pump 222 in a closed initial state with the piston 239 closed and touching (or nearly so) the first piston 236.

FIG. 10 is a view of the tidal pump 222 with the nested pistons 236, 239 each displaced to form or open a first chamber 250 and a second chamber 252 during pumping. The first chamber 250 draws liquid from the squeezing of the implants and the chamber 252 draws liquid from the reservoir 224.

FIG. 11 is a view of the tidal pump 222 with the first chamber 250 and the second chamber 252 in an orientation that has filled the chamber 250 with liquid from the implants and chamber 252 with liquid from the reservoir 224 during pumping (from squeezing the implants) prior to delivering the amplified liquid to the implants.

With reference to FIG. 8 through FIG. 11, the tidal pump 222 (or pump 222) includes a housing 230 having an inlet end 232 attachable to the reservoir 224 and an outlet end 234 attachable to an inflatable penile implant(s). The tubing coupled to the implants and the reservoir 224, and the tubing coupled between the pump 222 and the reservoir 224, are not illustrated but are similar to that shown in FIG. 1.

The first piston 236 is biased within the housing 230, and the second piston 239 biased within the housing 230, where the first piston 236 and the second piston 239 are each movable within the housing 230 and the second piston 239 is nested inside of the first piston 236. In one embodiment, the first piston 236 and the second piston 239 are co-axial. The second piston 239 is biased by a return spring 238.

A pulley strap 260, described below, mechanically couples the second piston 239 with the first piston 236 such that the bias force on the first piston 236 is double the spring force on the second piston 239. In one example, the pulley strap 260 has a first portion exterior to the first piston 236 and a second portion interior to the first piston 236 that couples with the second piston 239, as shown toward the inlet end 232 of the pump 222 in FIG. 8.

A first check valve 240 or lower check valve 240 is formed in the face 241 of the piston 236 adjacent to the outlet end 234. A second check valve 242 or upper check valve 242 is positioned at a leading portion of the piston 239 to communicate with the inlet end 232 of the housing 230. In one embodiment, the second check valve 242 is an O-ring check valve. In an alternative embodiment, the second check valve 242 is located within a face of the second piston 239.

In FIG. 10, a displacement of the piston 236 away from the outlet end 234 of the housing 230 forms a first chamber 250 communicating with the penile implant 226 and a second chamber 252 communicating with the reservoir 224. The piston 236 is displaced when a first volume of liquid is moved from the penile implant 226 into the first chamber 250, and the displacement of the first piston 236 results in a displacement of the second piston 239 by the pulley strap 260, described in detail below. The liquid entering the first chamber 250 is prevented from moving into the second chamber 252 by the first check valve 240. The displacement of the first piston 236 displaces the second piston 239, and this forms a suction within the second chamber 252 that draws a second volume of liquid from the reservoir 224 and into the second chamber 252. The liquid in the second chamber 252 is prevented from moving back to the reservoir 224 by the second check valve 242. When the nested pistons 236, 239 are moved back toward the outlet end 234 of the housing 230, the liquid in the second chamber 252 passes through the first check valve 240, and both the first volume of liquid and the second volume of liquid are delivered into the penile implant 226.

In this embodiment, the second piston 239 is attached to the housing 230 by the strap 260 or pulley connection. The strap 260 is coupled to the second piston 239 at a first end 262 of the strap 260 and to the housing 230 at an opposite second end 264 of the strap 260 (See FIG. 8). As shown in FIG. 8, the first piston 236 is disposed between a first section 263 of the pulley strap 260 that terminates in the first end 262 and a second section 265 of the pulley strap that terminates in the second end 264. As the first piston 236 moves to the right, it will push the mid-portion of the strap 260 to the right and away from the housing 230, as shown in FIGS. 10-11. The displacement of the first piston 236 results in the second piston 239 also displacing to the right, since the second piston 239 is "pulled" by the first end of the strap 260. Thus, movement of the first piston 236 is followed by movement of the second piston 239, and the movement is accomplished without a spring bias for the first piston 236 as it is replaced by the mid-portion of the strap 260.

The housing 230 is a telescoping housing that is compact when implanted (with a length T1 in FIG. 9), but during use, the first piston 236 telescopes or extends to increase an overall length of the housing (T2 in FIG. 10 and T3 in FIG. 11, where T3>T2>T1). In one embodiment, a container may be placed around the tidal pump 222 to allow expansion of the housing 230 without interaction with nearby tissue. A shell or container around the tidal pump 222 would allow the repeat expansion/contraction of the housing 230 without poking or pinching adjacent tissue.

The nested pistons 236, 239 locate the first chamber to be co-axial with the second chamber 252, which beneficially makes the pump 222 shorter for implantation. When the nested pistons 236, 239 are compressed together, the total length is reduced, which is useful when the surgeon implants the pump 222. Naturally, when the nested pistons 236, 239 expand, axial space is occupied, so the surgeon will take this into account. The pulley strap 260 biases the first piston 236 during its stroke, and thus the spring constant of the spring 238 may beneficially be of a smaller value (the force to displace the spring can be smaller), which allows the spring 238 to be smaller in size. In some embodiments, the spring constant for the spring 238 may be specified to be half of the spring constant of the spring 38 described above due to the mechanical advantage of the pulley system.

The pump 222 can be configured to perform similarly to the tidal pump 22 by utilizing or optimizing the ratio of the diameters of the piston 236, 239 along with a tuned selection of a spring constant for spring 238. As one example of the performance of the tidal pump 222, the fluid amplification for a squeeze pressure of 10 psi is about 0.2 cc per squeeze. The liquid amplification (in the case of saline liquid) can be adjusted by adjusting the proportional volumes of the first chamber 250 relative to the volume of the second chamber 252.

In general, the tidal pumps 22, 122 and 222 can be configured identically by selecting appropriate area ratios of the two pistons (which affect the sizes of the chambers) and spring constant for each embodiment. In some cases, tidal pump 22 will have advantages over other such tidal pumps when comparing main spring size and body compactness.

A variety of tidal pumps are described. A method of inflating a penile implant by utilizing any of the tidal pumps includes:
providing the inflatable penile prosthesis and configuring the inflatable penile prosthesis to operate such that:
1) squeezing the penile implant increases a pressure of liquid in the penile implant thus moving a first volume of the liquid from the penile implant into the first chamber;
2) displacing the first piston away from the outlet end of the housing with the first volume of liquid and forming a suction in the second chamber;
3) drawing a second volume of liquid out of the reservoir and into the second chamber; and
4) biasing the first piston toward the outlet end of the housing with the return spring and moving first volume of liquid and the second volume of liquid into the penile implant.

The providing of the inflatable penile prosthesis includes providing an implant in a package along with instructions for implantation and use.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention is limited only by its claims and their equivalents.

What is claimed is:

1. An inflatable penile prosthesis comprising a pump coupled in fluidic communication between a reservoir and a penile implant, the pump comprising:
    a housing having an inlet end communicating with the reservoir and an outlet end attachable to the penile implant;
    a first piston biased within the housing by a return spring such that a displacement of the first piston away from the outlet end of the housing forms a first chamber communicating with the penile implant and forms a second chamber communicating with the reservoir;
    a first check valve positioned between the first chamber and the outlet end; and
    a second check valve positioned between the second chamber and the inlet end;
    configured such that:
        a) moving a first volume of liquid from the penile implant displaces the first piston and transfers the first volume of liquid into the first chamber,
        b) displacement of the first piston creates a suction within the second chamber that draws a second volume of liquid from the reservoir and into the second chamber, and
        c) a return of the first piston toward the outlet end of the housing moves the first volume of liquid and the second volume of liquid into the penile implant.

2. The pump of claim 1, wherein the first chamber is located between a face of the piston and the outlet end of the housing, and the second chamber is located between a side wall of the piston and an internal wall of the housing.

3. The pump of claim 2, wherein the first check valve is formed in the face of the piston, and the second check valve seals a trailing end of the piston relative to the internal wall of the housing.

4. The pump of claim 1, wherein the first chamber is co-axial with the second chamber.

5. The pump of claim 1, further comprising:
    a second piston within the housing, where the first piston and the second piston are oriented side-by-side and the first chamber is separated from the second chamber.

6. The pump of claim 5, wherein the first check valve is located between the first piston and the second piston, and the second check valve is located between the reservoir and the housing.

7. The pump of claim 1, wherein the first chamber is co-axial with the second chamber, and further comprising:
    a second piston biased within the housing, where the first piston and the second piston are each movable within the housing and the second piston is nested inside of the first piston.

8. The pump of claim 7, wherein the second piston is coupled with the first piston by a pulley strap.

9. The pump of claim 8, wherein the pulley strap has a first end coupled to the second piston and a second end coupled to the housing.

10. The pump of claim 9, wherein the first piston is disposed between a first section of the pulley strap that terminates in the first end of the pulley strap and a second section of the pulley strap that terminates in the second end of the pulley strap.

11. An inflatable penile prosthesis comprising a pump coupled in fluidic communication between a reservoir and a penile implant, the pump comprising:
   a housing having an inlet end adapted to communicate with the reservoir and an outlet end adapted to communicate with the penile implant;
   a first piston retained in and biased relative to the housing, where displacement of the first piston within the housing forms a first chamber that communicates with the penile implant and a suction chamber that communicates with the reservoir;
   a first check valve disposed between the first chamber and the penile implant; and
   a second check valve disposed between the suction chamber and the reservoir;
   wherein movement of an implant liquid out of the penile implant is adapted to:
      a) displace the first piston within the housing to allow the implant liquid to enter the first chamber, and
      b) create suction within the suction chamber to draw a reservoir liquid from the reservoir into the suction chamber;
   wherein a return of the first piston within the housing pushes the implant liquid though the first check valve and pushes the reservoir liquid through the second check valve, with both the implant liquid and the reservoir liquid moving into the penile implant.

12. The pump of claim 11, wherein the first chamber is located between a face of the first piston and the outlet end of the housing, and the suction chamber is located between a side wall of the first piston and an internal wall of the housing.

13. The pump of claim 11, further comprising:
   a second piston within the housing, where the first piston and the second piston are oriented side-by-side;
   wherein the first chamber is located between a face of the first piston and the outlet end of the housing and the suction chamber is located between a face of the second piston and the inlet end of the housing.

14. The pump of claim 13, wherein the first check valve is located between the first piston and the second piston, and the second check valve is located between the reservoir and the housing.

15. The pump of claim 11, wherein the first chamber is co-axial with the suction chamber, and further comprising:
   a second piston biased within the housing, where the first piston and the second piston are each movable within the housing, with the second piston co-axial with the first piston, and the second piston is coupled with the first piston by a pulley strap.

16. An inflatable penile prosthesis comprising a pump coupled in fluidic communication between a reservoir and a penile implant, the pump comprising:
   a housing having an external wall, an internal wall, an inlet end attachable to the reservoir, and an outlet end attachable to the penile implant;
   a piston inserted in the housing, with the piston having a face end oriented toward the outlet end of the housing and a trailing end oriented toward the inlet end of the housing;
   a return spring connected between the trailing end of the piston and the inlet end of the housing;
   a first fluid chamber located between the face end of the piston and the outlet end of the housing; and
   a second fluid chamber located between the piston and the internal wall of the housing.

17. The pump of claim 16, further comprising:
   a first check valve disposed between the first fluid chamber and the penile implant.

18. The pump of claim 16, further comprising:
   a second check valve disposed between the second fluid chamber and the reservoir.

* * * * *